US010608418B2

(12) United States Patent
Damazo et al.

(10) Patent No.: US 10,608,418 B2
(45) Date of Patent: Mar. 31, 2020

(54) SPARK-BASED COMBUSTION TEST SYSTEM (71) Applicant: THE BOEING COMPANY, Chicago, IL (US)

(72) Inventors: Jason S. Damazo, Seattle, WA (US); Eddie Kwon, Seattle, WA (US); Philipp A. Boettcher, Philadelphia, PA (US)

(73) Assignee: THE BOEING COMPANY, Chicago, IL (US)

( * ) Notice: Subject to any disclaimer, the term of this patent is extended or adjusted under 35 U.S.C. 154(b) by 222 days.

(21) Appl. No.: 15/899,053

(22) Filed: Feb. 19, 2018

(65) Prior Publication Data
US 2019/0260184 A1 Aug. 22, 2019

(51) Int. Cl.
H01T 13/50 (2006.01)
G01N 25/28 (2006.01)
H01T 13/02 (2006.01)
H01T 19/00 (2006.01)
F02P 17/00 (2006.01)
H05H 1/52 (2006.01)
(Continued)

(52) U.S. Cl.
CPC ............. H01T 13/50 (2013.01); F02P 17/00 (2013.01); G01N 25/28 (2013.01); G01N 25/52 (2013.01); H01T 13/02 (2013.01); H01T 19/00 (2013.01); H05H 1/52 (2013.01); F23Q 3/00 (2013.01); H01T 19/04 (2013.01); H05H 2001/481 (2013.01)

(58) Field of Classification Search
CPC ......... H01T 13/02; H01T 13/50; H01T 19/00; H01T 19/04; H05H 1/52; H05H 2001/481; F02P 17/00; F23Q 3/00; G01N 25/28; G01N 25/52
See application file for complete search history.

(56) References Cited

U.S. PATENT DOCUMENTS 6,205,309 B1 * 3/2001 Gundlach ............... H01T 19/00 250/324
9,341,610 B1 * 5/2016 McIver .................. G01N 33/22
(Continued)

OTHER PUBLICATIONS

Albert Baldebey Domènech, Control of a High Frequency Ignition System Based in Corona Discharge With Arduino, Apr. 26, 2017, ETSEIB, 83 pages (Year: 2017).*
(Continued)

Primary Examiner — Francis C Gray
(74) Attorney, Agent, or Firm — Moore IP Law (57) ABSTRACT A combustion test system includes a power source and a corona generator coupled to the power source. The combustion test system also includes a charge storage device. The charge storage device includes a charging surface spaced apart from the corona generator such that charge carriers, motivated by an electric field of the corona generator, intersect the charging surface to charge the charge storage device. The combustion test system also includes a first electrode coupled to the charge storage device and a second electrode coupled to a reference ground. The second electrode is spaced apart from the first electrode to produce an electrical arc between the first electrode and the second electrode based on a voltage difference between the first electrode and the second electrode.

20 Claims, 4 Drawing Sheets (51) Int. Cl.
*G01N 25/52* (2006.01)
*H01T 19/04* (2006.01)
*H05H 1/48* (2006.01)
*F23Q 3/00* (2006.01)

(56) References Cited

U.S. PATENT DOCUMENTS

| | | |
|---|---|---|
| 9,514,917 B1 | 12/2016 | McIver et al. |
| 2006/0187609 A1* | 8/2006 | Dunn ........................ B03C 3/09 361/230 |
| 2014/0358399 A1* | 12/2014 | Schremmer ............. F02P 17/00 701/101 |

OTHER PUBLICATIONS

Extended European Search Report for application No. 18211778.8 dated Jun. 17, 2019, 9 pgs.
Buhler, Charles, et al., "Test methodology to evaluate the safety of materials using spark incendivity", Journal of Electrostatics, Elsevier Science Publishers, vol. 64, 2006, pp. 744-751.
Fisher, F. "Some Notes on Sparks and Ignition of Fuels," NASA/TM-2000-210077, Lightning Technologies Inc., Pittsfield, MA, Mar. 2000, 40 pgs.
Shepherd, J. et al., "Spark Ignition Energy Measurements in Jet A," Explosion Dynamics Laboratory Report FM97-9, Graduate Aeronautical Laboratories, California Institute of Technology, Pasadena, CA, Jan. 24, 2000, 87 pgs.

\* cited by examiner

SPARK-BASED COMBUSTION TEST SYSTEM

FIELD

The present disclosure generally relates to devices, systems, and methods for spark-based combustion testing.

BACKGROUND

Low energy electrical arcs are used as ignition sources in various industrial and academic test systems, such as in systems that test flammability properties of materials. For example, an electrical arc may be used as an ignition source to measure the ignitability of a gas or a gaseous mixture, such as a fuel-air mixture. Generally, the electrical arc is generated by a sparking device that includes electrodes that are spaced apart from one another. A material to be tested is disposed in a region between the electrodes, and a voltage is applied to the electrodes. The electrical arc is generated between the electrodes when the voltage across the electrodes exceeds a breakdown voltage of the material to be tested.

For some tests, the energy level of the electrical arc must be carefully controlled to fall within a specified range. For example, a test procedure that the Federal Aviation Administration (FAA) requires for testing the ignitability of fuel-air mixtures used for aircraft calls for the use of an electrical arc of 200 microjoules plus 0 microjoules minus 20 microjoules. Due to the short duration and very low energy levels of such electrical arcs, direct measurement of the energy level of the electrical arcs is not generally possible. This has led academic and industrial testing to focus on the stored potential electrical energy that may contribute to an electrical arc as the quantity to which to calibrate flammable gas ignitability rather than the actual energy dissipated in the electrical arc channel itself.

In many test systems, the energy storage system uses a capacitor to store the energy. At such low energy levels (e.g., in the 100 microjoule range) and with such tight tolerances (e.g., several microjoules), minor changes in circuitry coupled to the sparking device can result in significant changes in the energy of the electrical arc. For example, the breakdown voltage of a fuel-air mixture may be on the order of kilovolts. To provide a voltage across electrodes of the sparking device on the order of kilovolts with a total energy storage on the order of microjoules requires a capacitance on the order of picofarads. At such small capacitances, the capacitance of the entire circuit coupled to the sparking device must be taken into account since changes as minor as shifting the relative positions of two wires can cause changes in the capacitance of the circuit that effect the test. As a result, testing systems that use low energy, high precision electrical arcs are notoriously difficult to use.

SUMMARY

In a particular embodiment, a combustion test system includes a power source and a corona generator coupled to the power source. The combustion test system also includes a charge storage device including a charging surface spaced apart from the corona generator such that charge carriers, motivated by an electric field of the corona generator, intersect the charging surface to charge the charge storage device. The combustion test system further includes a first electrode coupled to the charge storage device and a second electrode coupled to a reference ground. The second electrode is spaced apart from the first electrode to produce an electrical arc between the first electrode and the second electrode based on a voltage difference between the first electrode and the second electrode.

In another particular embodiment, a method includes storing a charge at a charge storage device responsive to charge carriers that are directed toward the charge storage device responsive to an electric field of a corona generator. The method also includes generating a voltage difference between a first electrode coupled to the charge storage device and a second electrode coupled to a reference ground. The method further includes producing an electrical arc between the first electrode and the second electrode based on the voltage difference between the first electrode and the second electrode.

In another particular embodiment, a spark generation device includes a charge storage device including a charging surface configured to store charge responsive to charge carriers motivated by an electric field of a corona generator. The spark generation device also includes a first electrode coupled to the charge storage device and a second electrode coupled to a reference ground. The second electrode is spaced apart from the first electrode to produce an electrical arc between the first electrode and the second electrode based on a voltage difference between the first electrode and the second electrode.

The described features, functions, and advantages may be achieved independently in various embodiments or may be combined in yet other embodiments further details of which can be seen with reference to the following description and drawings.

DETAILED DESCRIPTION

As used herein, various terminology is used for the purpose of describing particular implementations only and is not intended to be limiting of implementations. For example, the singular forms "a," "an," and "the" are intended to include the plural forms as well, unless the context clearly indicates otherwise. It may be further understood that the terms "comprise," "comprises," and "comprising" may be used interchangeably with "include," "includes," or "including." Additionally, it will be understood that the term "wherein" may be used interchangeably with "where." As used herein, "exemplary" may indicate an example, an implementation, and/or an aspect, and should not be construed as limiting or as indicating a preference or a preferred implementation. As used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). As used herein, the term "set" refers to one or more of a particular element, and the term "plurality" refers to multiple (e.g., two or more) of a particular element.

Implementations disclosed herein electrically isolate a charge storage device that is used to produce an electrical arc from a power source that charges the charge storage device. A physical gap is disposed between the charge storage device and circuitry associated with the power source. No physical conductor connects a charging surface of the charge storage device to the power source and associated circuitry. This physical gap provides electrical isolation of the charge storage device such that changes in the power source and associated circuitry do not change the energy storage capacity of the charge storage device.

The charge storage device is charged using a corona generator that is coupled to the power source. The corona generator generates charge carriers that carry charge to the charge storage device across the gap. The corona generator generates a relatively strong electric field in some regions, which is sufficient to ionize gases in the gap to liberate the charge carriers. The gap effectively allows energy to move from the corona generator to the charge storage device, but prevents movement of energy from the charge storage device back to the corona generator. Accordingly, the energy storage capacity of the charge storage device can be determined (though calibration or calculation) independently of the power source, the corona generator, and associated circuitry. Thus, a combustion test system based on the present disclosure is able to reliably produce low energy, high precision electrical arcs with less concern for changes to the power source and associated circuitry.

Figure 1:
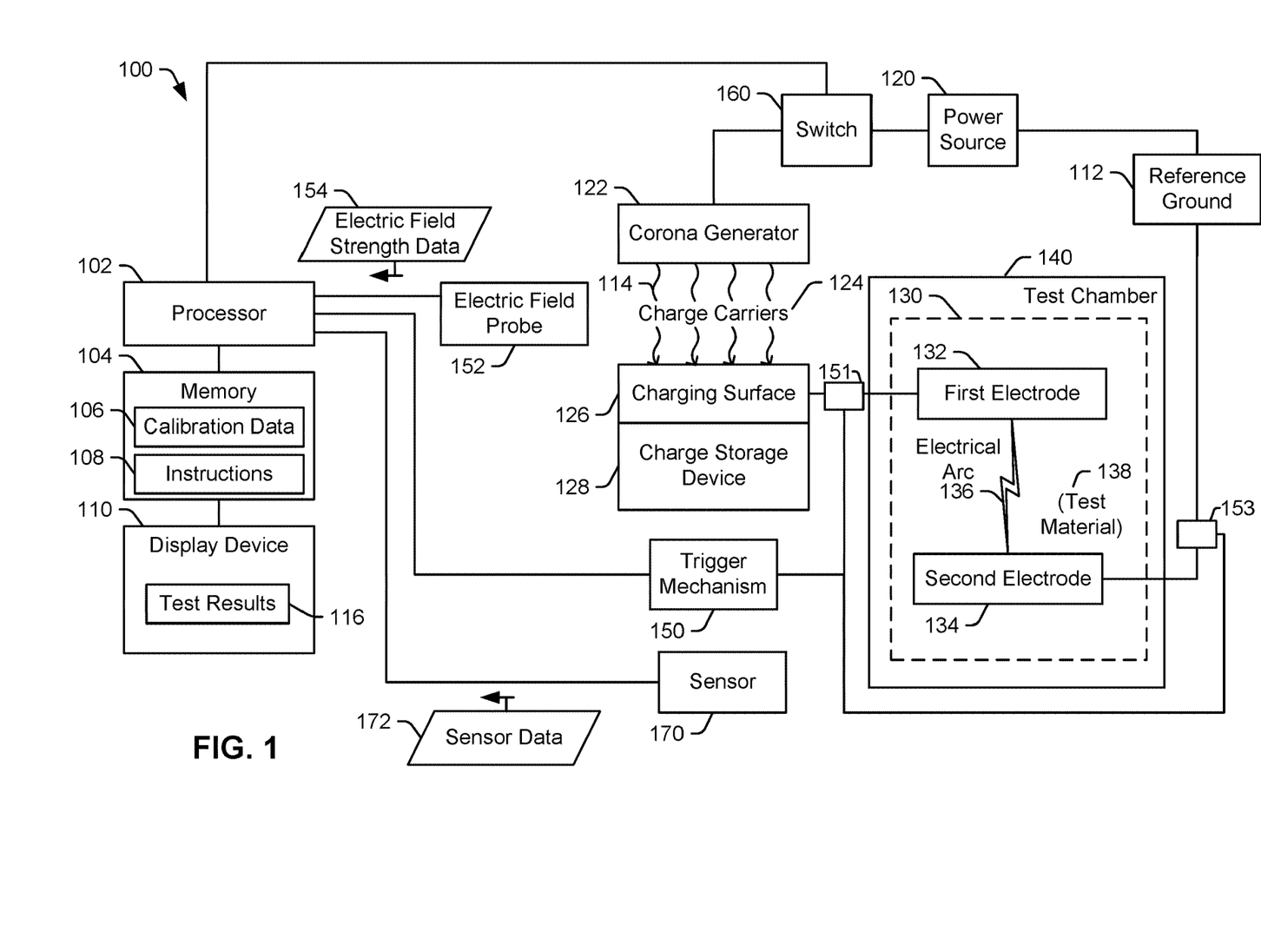
FIG. 1 is a block diagram illustrating a particular implementation of a combustion test system.

FIG. 1 is a block diagram illustrating a particular implementation of a combustion test system 100. The combustion test system 100 includes a spark generation device 130 that includes a first electrode 132 and a second electrode 134 spaced apart from one another (i.e., not in direct physical contact with one another). A material to be tested, such as test material 138, is disposed in a region between the first electrode 132 and the second electrode 134. In the particular implementation illustrated in FIG. 1, the test material 138 and the spark generation device 130 are disposed within a test chamber 140. The test chamber 140 protects the test material 138 from contaminants. Further, if the test material 138 is a gas or gaseous mixture, the test chamber 140 retains the test material 138 and enables control of test properties such as the pressure and/or the temperature of the test material 138.

As explained further below, the spark generation device 130 is configured to generate an electrical arc 136 between the first and second electrodes 132, 134 when a voltage difference between the first and second electrodes 132, 134 exceeds a threshold, such as a breakdown voltage of the test material 138. When the combustion test system 100 is used to generate test results 116 based on some test protocols, the electrical arc 136 is a very low energy arc (e.g., approximately hundreds of microjoules, such as about 200 microjoules for certain FAA certification tests) and has a narrow range of acceptable values (e.g., plus or minus a few tens of microjoules, such as up to minus 20 microjoules for the above referenced FAA certification tests). However, as previously explained, direct measurement of the electrical arc 136 is difficult. Accordingly, the energy of the electrical arc 136 may be estimated based on energy available from a charge storage device 128 to form the electrical arc 136. The combustion test system 100 is arranged to electrically isolate the charge storage device 128 from other circuitry, such as a power source 120, a reference ground 112, and related circuitry. By electrically isolating the charge storage device 128 from the other circuitry, changes in the other circuitry do not change the energy storage capacity of the charge storage device 128. Thus, after calibration of the charge storage device 128, the energy stored at the charge storage device 128 can be reliably known even if changes are made to the other circuitry.

In the example illustrated in FIG. 1, the second electrode 134 is coupled to the reference ground 112, and the first electrode 132 is coupled to the charge storage device 128. The charge storage device 128 includes a charging surface 126, which is spaced apart from (i.e., not in direct physical contact with) a corona generator 122. The corona generator 122 is coupled to the power source 120. The corona generator 122 is configured to charge the charge storage device 128 while electrically isolating the charge storage device 128 (or at least the charging surface 126) from circuitry associated with the corona generator 122, the power source 120, the reference ground 112, and the second electrode 134. Thus, the charging surface 126 is electrically isolated from the power source 120 and is electrically isolated from the reference ground 112. Stated another way, no conductor or set of conductors connects the charging surface 126 to the power source 120 or to the reference ground 112, and a voltage of the charging surface 126 of the charge storage device 128 is free to float.

To charge the charge storage device 128, the power source 120 applies a voltage to the corona generator 122, and the corona generator 122 generates an electric field 114 responsive to the voltage. The power source 120 can be a direct current (DC) power supply, an alternating current (AC) power supply, or a hybrid power supply that provides DC-biased alternating current. Thus, a polarity of the voltage applied by the power source 120 can be time varying (e.g., the polarity alternates between a positive polarity and a negative polarity), or the polarity of the voltage can be non-time varying (e.g., the polarity, though not necessarily the magnitude, of the voltage is constant over time).

The corona generator 122 includes a conductor or conductors with geometric features (such as a point or sharp curvature) that form a region of high potential gradient of the electric field 114 responsive to the voltage. A corona 202 (shown in FIGS. 2 and 3) forms in the region of high potential gradient of the electric field 114 when the electric field 114 ionizes gases (e.g., stripping electrons from the gases) near the corona generator 122. The ionized gases and electrons liberated by the ionization are charge carriers 124. Each charge carrier 124 has a charge that interacts with the electric field 114 of the corona generator 122 to either cause the charge carrier 124 to move toward the corona generator 122 or to move away from the corona generator 122. The charging surface 126 is positioned such that either positive charge carriers (e.g., gas ions) or negative charge carriers (e.g., electrons) motivated by an electric field 114 of the corona generator 122 intersect the charging surface 126 to charge the charge storage device 128. In some implementations, the corona generator 122 includes one or more conductive grids between the corona generating conductor or conductors and the charging surface. In such implementations, the conductive grid can be charged by application of a bias voltage to facilitate or control movement of the charge carriers 124 toward the charging surface 126.

Since the voltage of the charging surface 126 floats, electrical potential of the charging surface 126 increases as charge carriers 124 intersect the charging surface 126, and energy is stored at the charge storage device 128. As the electrical potential of the charging surface 126 increases, the electrical potential of the charging surface 126 opposes the electric field 114 of the corona generator 122 and may eventually limit further generation of charge carriers 124 or deflect additional charge carriers 124, such that charging of the charge storage device 128 is automatically self-limiting. Thus, in some implementations, energy stored at the charge storage device 128 is highly repeatable and self-regulating.

Alternatively or in addition, the combustion test system 100 may include a switch 160 or another control element that can be controlled to control energy stored at the charge storage device 128. For example, in FIG. 1, the combustion test system 100 includes an electric field probe 152 positioned to measure an electric field strength of the electric field 114 or of a portion of the electric field 114. In this example, the electric field probe 152 provides electric field strength data 154 to a processor 102, and the processor 102 analyzes the electric field strength data 154 based on calibration data 106 in a memory 104 accessible to the processor 102. The processor 102, in this example, is coupled to the switch 160 and configured to actuate the switch 160 based on the calibration data 106 and the electric field strength data 154. To illustrate, the processor 102 may determine, based on the calibration data 106 and the electric field strength data 154, when charge storage device 128 has been charged to a threshold energy level and may actuate the switch 160 in response to determining that the charge storage device 128 has been charged to the threshold energy level.

In the example illustrated in FIG. 1, the first electrode 132 of the spark generation device 130 is coupled to the charging surface 126, and the second electrode 134 of the spark generation device 130 is coupled to the reference ground 112. As the charge storage device 128 is charged, a voltage difference between the first electrode 132 and the second electrode 134 increases. The electrical arc 136 is produced based on the voltage difference between the first electrode 132 and the second electrode 134 (e.g., when the voltage difference satisfies a threshold). Whether the voltage difference is sufficient to generate the electrical arc 136 depends, among other things, on a distance between the first and second electrodes 132, 134, characteristics of the test material 138, pressure within the test chamber 140, and whether additional energy is added from another source, such as a trigger mechanism 150. For a given test set up, the threshold is related to, but may not be identical to, a breakdown voltage of a portion of the test material 138 between the first and second electrodes 132, 134.

In some implementations, the trigger mechanism 150 is used as a source of excitation energy to initiate the electrical arc 136. To illustrate, in such implementations, the trigger mechanism 150 can include a laser source or high energy light source that provides the excitation energy as light. In other implementations, the trigger mechanism 150 initiates the electrical arc 136 by changing a test condition, such as by injecting the test material 138 into the test chamber 140 or by moving the first electrode 132 and the second electrode 134 closer together. In yet other implementations, the trigger mechanism 150 includes a switch 151 to selectively electrically connect the charging surface 126 to the first electrode 132, a switch 153 to selectively electrically connect the second electrode 134 to the reference ground 112, or both. In the example illustrated in FIG. 1, the trigger mechanism 150 is coupled to the processor 102 and is controlled responsive to signals from the processor 102. In other examples, the trigger mechanism 150 is manually activated (e.g., by an operator of the combustion test system 100) or is coupled to and controlled by a different processor (not shown).

The processor 102, in the example illustrated in FIG. 1, is also configured to generate the test results 116. For example, the processor 102 is coupled to a sensor 170 disposed within or proximate to the test chamber 140. In this example, the sensor 170 generates sensor data 172 indicating a result of the electrical arc 136. To illustrate, the sensor 170 can include an image sensor that generates one or more images depicting a portion of an interior of the test chamber 140. In this illustrative example, the one or more images may include multiple frames of video before, during, and after the electrical arc 136 is generated. The processor 102 is configured to execute instructions 108 from the memory 104 to analyze the sensor data 172 and to generate the test results 116. In some implementations, the test results 116 may be presented an operator of the combustion test system 100 via a display device 110.

During operation of the combustion test system 100, the power source 120 is activated and coupled to the corona generator 122 (e.g., by actuating the switch 160). Voltage applied to the corona generator 122 by the power source 120 causes the corona generator 122 to generate the electric field 114. The electric field 114 ionizes gases proximate to the corona generator 122 to liberate the charge carriers 124. Some of the charge carriers 124 are motivated, by interaction with the electric field 114, toward the charging surface 126. Charge carriers 124 that intersect the charging surface 126 convey charge to the charging surface 126, thereby increasing electrical potential of the charging surface 126. Eventually, energy stored at the charge storage device 128 is sufficient (e.g., meets a threshold) and the electrical arc 136 is initiated, as described further below. In some implementations, the amount of energy stored at the charge storage device 128 when the threshold is met is self-regulating. In other implementations, the amount of energy stored at the charge storage device 128 is estimated by the processor 102 based on the electric field strength data 154 and the calibration data 106, and the processor 102 determines when the threshold is met.

Before, during, or after charging the charge storage device 128, the test material 138 is introduced into the test chamber 140. In some implementations, the test material 138 is introduced into the test chamber 140 before or during charging of the charge storage device 128. For example, if the test procedure requires controlling the pressure and temperature within the test chamber 140, the test material 138 may be introduced before or during charging of the charge storage device 128 to allow time for transient conditions associated with the pressure and temperature to level out.

After conditions within the test chamber 140 meet requirements of the test procedure and after the charge storage device 128 is charged, the electrical arc 136 is initiated. For example, the trigger mechanism 150 is activated to add excitation energy, to connect the first electrode 132 to the charge storage device 128, to connect the second electrode 134 to the reference ground 112, or to change relative positions of the first and second electrodes 132, 134. The sensor 170 provides the sensor data 172 to the processor 102, and the processor 102 analyzes the sensor data 172 to generate the test results 116. If the trigger mechanism 150 adds excitation energy to initiate the electrical arc 136, the excitation energy may be accounted for in determining the test results 116.

The charging surface 126 of the charge storage device 128 is electrically isolated from much of the other circuitry of the combustion test system 100. For example, the charging surface 126 is not conductively coupled to circuitry associated with the corona generator 122, the switch 160, the power source 120, and the reference ground 112. This electrical isolation means that changes to the other circuitry of the combustion test system 100 do not change the energy storage capacity of the charge storage device 128. Accordingly, the combustion test system 100 is much easier to work with than combustion test systems in which the charge storage device is electrically connected to other circuits of the combustion test system 100. For example, the power source 120 of the combustion test system 100 can be removed and replaced with a different power source (even a different type of power source) without changing the energy storage capacity of the charge storage device 128. Stated another way, the electrical isolation of the charging surface 126 means that charge stored at circuit elements that are electrically isolated from the charge storage device 128 can be ignored. In contrast, if the charge storage device 128 were electrically connected to the power source 120, changing the power source could significantly change the charge storage capacity of the circuitry of the combustion test system 100 in a manner that would affect the test results 116. For example, if the charge storage device 128 were electrically connected to the power source 120, changing the total capacitance of the circuitry of the combustion test system on the order of a few picofarads would change the amount of energy provided by the electrical arc 136 enough to affect (and possibly invalidate) the test results 116.

Figure 2:
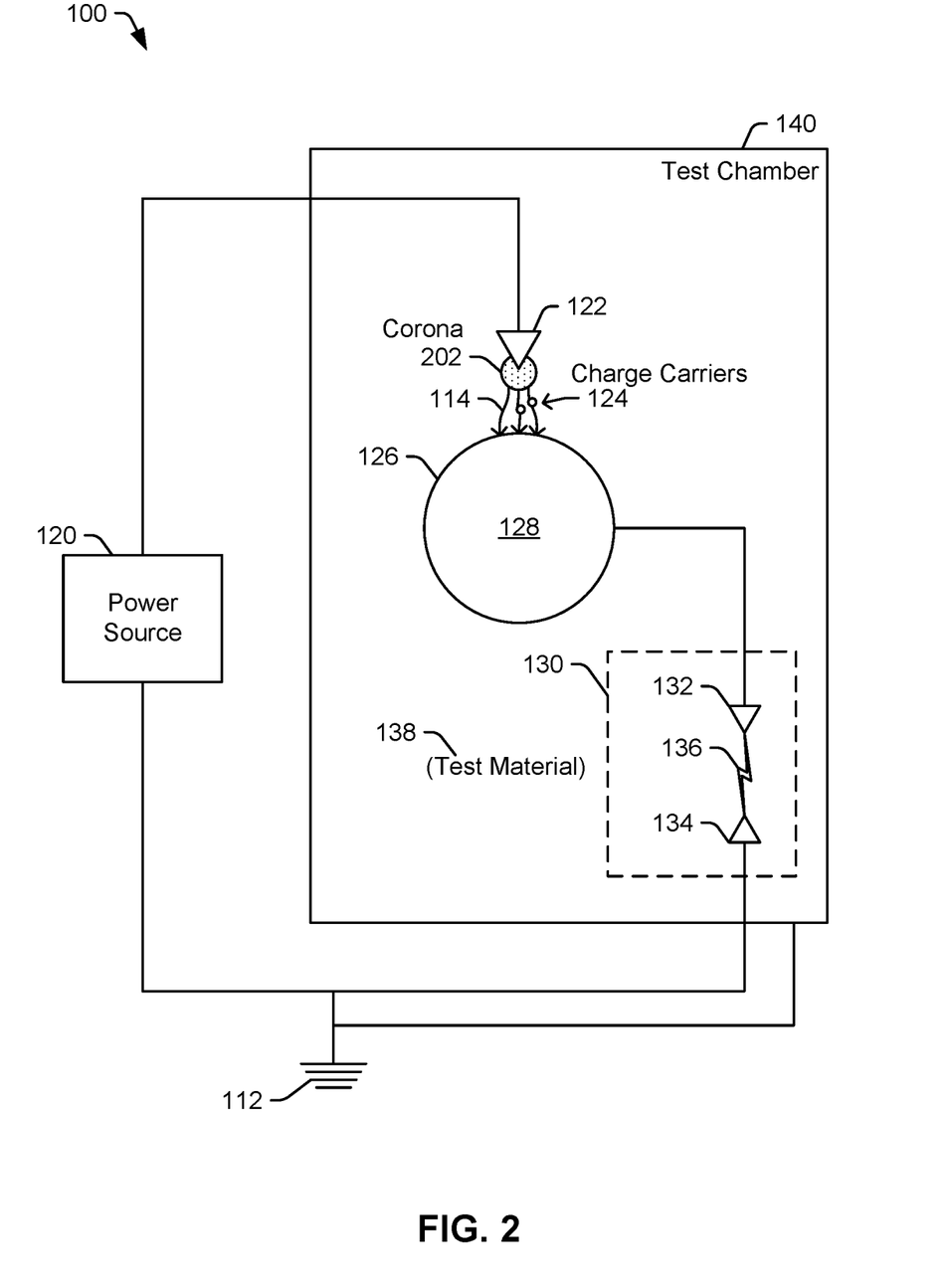
FIG. 2 is a schematic diagram of a particular implementation of the combustion test system of FIG. 1.

FIG. 2 is a schematic diagram of a particular implementation of the combustion test system 100 of FIG. 1. In FIG. 2, the combustion test system 100 includes the test chamber 140, the spark generation device 130, the power source 120, the reference ground 112, the corona generator 122, and the charge storage device 128 described with reference to FIG. 1. The combustion test system 100 may also include other features and components that are shown in FIG. 1 but are not shown in FIG. 2, such as the processor 102, the memory 104, the display device 110, the electric field probe 152, the trigger mechanism 150, the sensor 170, the switch 160, or a combination thereof.

In the implementation illustrated in FIG. 2, the charge storage device 128 is a conductive sphere, such as a hollow metal sphere, a solid metal sphere, or a metal-coated sphere of another material (e.g., glass or plastic). In this implementation, the charging surface 126 corresponds to a surface of the conductive sphere. The capacitance, C, of such a charging surface 126 can be calculated based on the radius, R, of the sphere and the electrical permittivity, E, of a material around the sphere using the equation $C=4\pi\varepsilon R$.

Although FIG. 2 illustrates the charge storage device 128 as a hollow conductive sphere, in other implementations other geometric arrangements and/or other materials may be used. In FIG. 2, the combustion test system 100 only needs the charge storage device 128 to store very small amounts of energy, thus the relative small storage capacity of the hollow conductive sphere of FIG. 2 is sufficient for some test procedures. The hollow conductive sphere has the advantage of having a capacitance that is readily quantifiable using the equation above. However, other geometric shapes, such as hollow conductive cubes, are also capable of storing charge and have a capacitance that is related to their geometry in a manner that is quantifiable mathematically or empirically. Thus, such other shapes may be used in some implementations.

Figure 3:
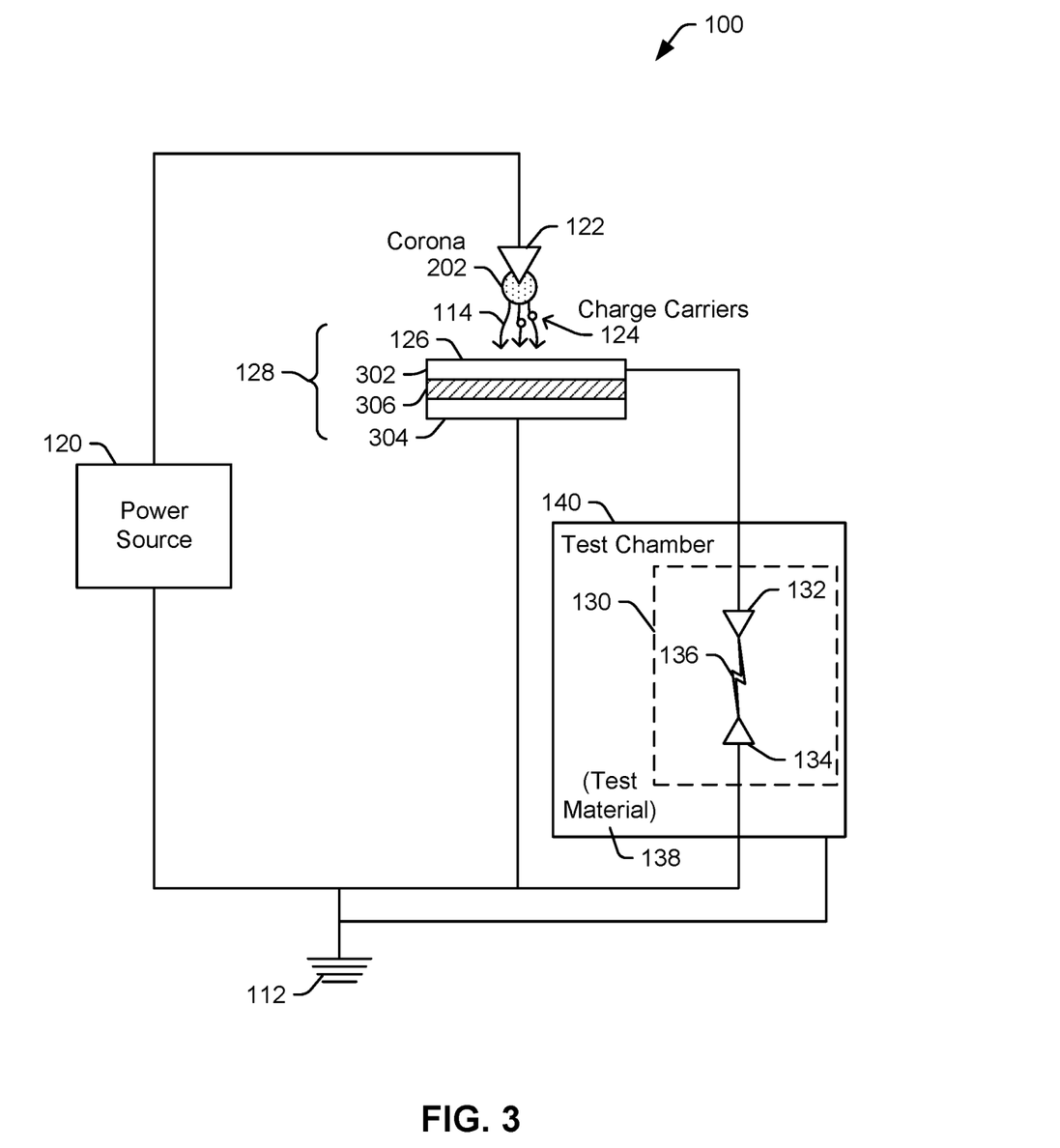
FIG. 3 is a schematic diagram of another particular implementation of the combustion test system of FIG. 1.

FIG. 3 is a schematic diagram of another particular implementation of the combustion test system 100 of FIG. 1. In FIG. 3, the combustion test system 100 includes the test chamber 140, the spark generation device 130, the power source 120, the reference ground 112, the corona generator 122, and the charge storage device 128 described with reference to FIG. 1. The combustion test system 100 may also include other features and components that are shown in FIG. 1 but are not shown in FIG. 3, such as the processor 102, the memory 104, the display device 110, the electric field probe 152, the trigger mechanism 150, the sensor 170, the switch 160, or a combination thereof.

In the implementation illustrated in FIG. 3, the charge storage device 128 is a capacitor. In this implementation, the charging surface 126 corresponds to or is coupled to a first capacitor electrode 302 of the capacitor. The first capacitor electrode 302 is separated from a second capacitor electrode 304 by a dielectric material 306. Although the charge storage device 128 is shown in FIG. 3 as a simple parallel plate capacitor, other types or arrangements of capacitors can be used. Further, although the charging surface 126 is illustrated in FIG. 3 as a component of the capacitor (e.g., as a surface of the first capacitor electrode 302), in some implementations, the charging surface 126 is distinct from, and electrically coupled to, the first capacitor electrode 302 of the capacitor.

In FIG. 3, the second capacitor electrode 304 of the capacitor is coupled to the reference ground 112, and the electrical potential of the charging surface 126 (or of the charging surface 126 and the first capacitor electrode 302) is free to float, as described with reference to FIG. 1. Using a capacitor as the charge storage device 128, as in FIG. 3, may enable storage of larger amounts of energy than using, for example, a hollow conductive sphere or other geometric shape, as in FIG. 2.

Figure 4:
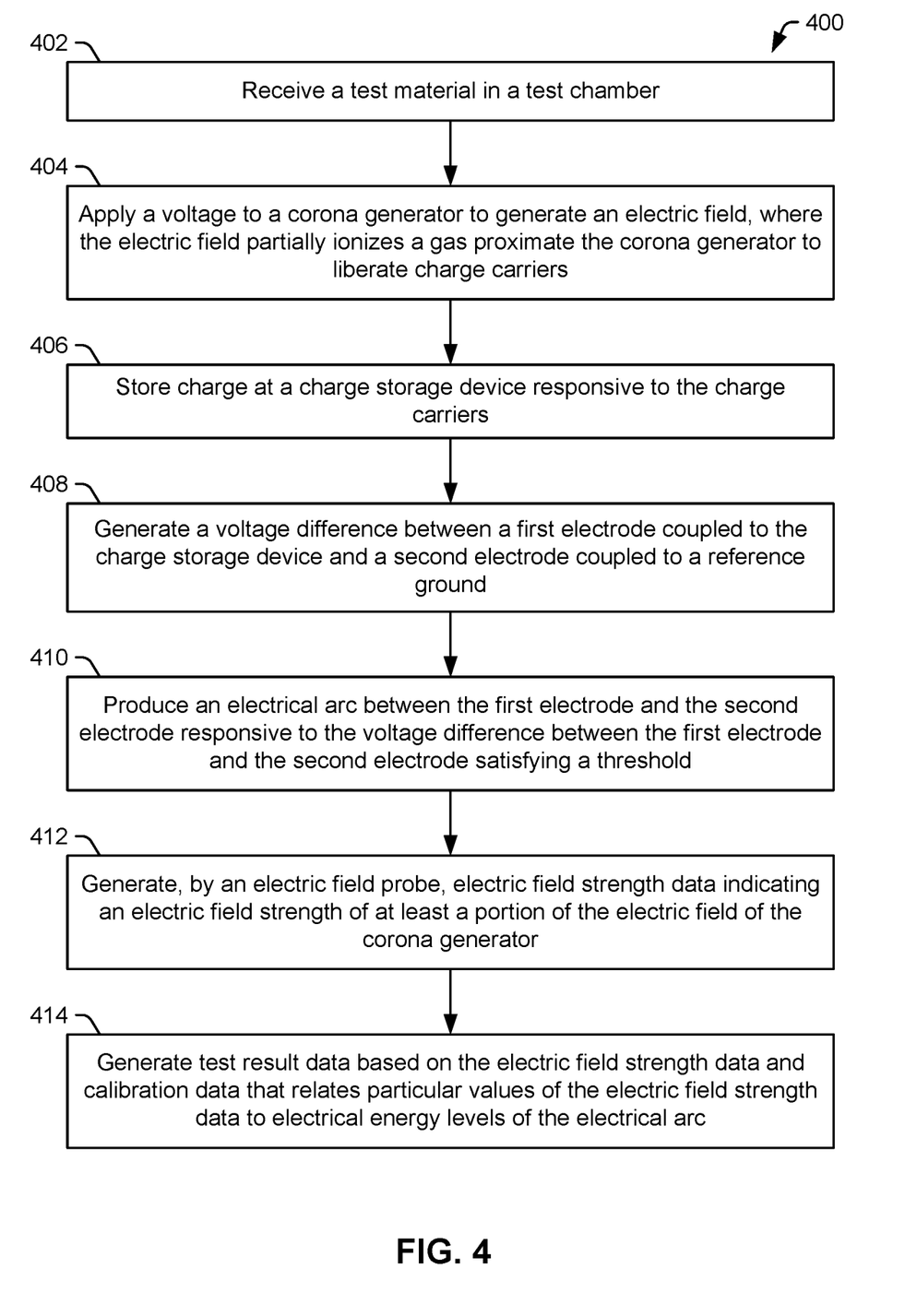
FIG. 4 is a flow chart illustrating a method of operation of the combustion test system of FIG. 1.

FIG. 4 is a flow chart illustrating a method 400 of operation of the combustion test system 100 of one or more of FIGS. 1-3. The method 400 includes, at 402, receiving a test material in a test chamber. For example, the test material 138 may be received in the test chamber 140 of FIGS. 1-3.

The method 400 also includes, at 404, applying a voltage to a corona generator to generate an electric field, where the electric field partially ionizes a gas proximate the corona generator to liberate charge carriers. For example, the power source 120 of FIGS. 1-3 may apply a voltage to the corona generator 122. In some implementations, a polarity of the voltage alternates over time, and in other implementations, the polarity of the voltage is constant over time. Responsive to the voltage, the corona generator 122 generates the electric field 114. The electric field 114 is of sufficient strength, at least in a region near the corona generator 122, to ionize gases near the corona generator 122, thereby liberating the charge carriers 124 (e.g., positively charged gas ions and negatively charged electrons).

The method 400 also includes, at 406, storing charge at a charge storage device responsive to the charge carriers, where at least some of the charge carriers are directed toward the charge storage device by the electric field of the corona generator. For example, the charge carriers 124 of FIGS. 1-3 liberated by the electric field 114 of the corona generator 122 are motivated due to interaction with the electric field 114. To illustrate, depending on the polarity of the voltage applied to the corona generator 122, negatively charged charge carriers either move away from the corona generator 122 or move toward the corona generator 122. Positively charged charge carriers move in a direction opposite the direction of movement of the negatively charged charge carriers. At least some of the charge carriers 124 that move away from the corona generator 122 intersect or impact the charging surface 126, thereby imparting a charge to the charge storage device 128.

The method 400 also includes, at 408, generating a voltage difference between a first electrode coupled to the charge storage device and a second electrode coupled to a reference ground. For example, as more of the charge carriers 124 of FIGS. 1-3 strike the charging surface, the amount of charge stored at (and therefore the electrical potential of) the charging surface 126 increases. In the implementations illustrated in FIGS. 1-3, the charging surface 126 is coupled to the first electrode 132. In such implementations, the increase in charge stored at the charging surface 126 also increases the charge stored at (and the electrical potential of) the first electrode 132. In some implementations, the trigger mechanism 150 includes the switch 151 between the charging surface 126 and the first electrode 132. In such implementations, the increase in charge stored and electrical potential of the charging surface 126 does not increase the charge stored at and the electrical potential of the first electrode 132 until the trigger mechanism 150 is actuated to close the switch 151. The second electrode 134 is coupled to the reference ground 112, and therefore has a relatively constant electrical potential. Accordingly, as the electrical potential of the first electrode 132 increases, while the electrical potential of the second electrode 134 remains relatively constant, a voltage difference is generated between the first electrode 132 and the second electrode 134.

The method 400 also includes, at 410, producing an electrical arc between the first electrode and the second electrode responsive to the voltage difference between the first electrode and the second electrode satisfying a threshold. The test material is subjected to the electrical arc. For example, the electrical arc 136 of FIGS. 1-3 is produced between the first electrode 132 and the second electrode 134 (and through the test material 138). The electrical arc 136 can be produced spontaneously when the voltage difference between the first electrode 132 and the second electrode 134 satisfies a threshold based on the breakdown voltage of the test material 138. Alternatively, the electrical arc 136 can be triggered (e.g., by the trigger mechanism 150) when the processor 102 determines that the energy level of the charge storage device 128 satisfies a threshold. To illustrate, electrical arc 136 can be triggered by closing the switch 151 to connect the first electrode 132 to the charging surface 126, by closing the switch 153 to couple the second electrode 134 to the reference ground 112, by moving the first and second electrodes 132, 134 closer together, or by adding excitation energy (e.g., via a laser or high intensity light source) into the test chamber 140.

The method 400 also includes, at 412, generating, by an electric field probe, electric field strength data indicating an electric field strength of at least a portion of the electric field of the corona generator. For example, the electric field probe 152 of FIG. 1 may measure a strength of the electric field 114 and generate the electric field strength data 154. In some implementations, the processor 102 uses the electric field strength data 154, along with the calibration data 106, to estimate an energy level of the charging surface 126. In such implementations, the processor 102 may determine, based on the electric field strength data 154 when the energy level of the charging surface 126 satisfies a threshold, such as a target energy level for a particular test procedure.

The method 400 also includes, at 414, generating test result data based on the electric field strength data and calibration data that relates particular values of the electric field strength data to electrical energy levels of the electrical arc. For example, the processor 102 of FIG. 1 may generate the test results 116 based on the sensor data 172, the electric field strength data 154 (or another estimate of the energy level of the charge storage device 128) when the electrical arc 136 is generated, and the calibration data 106.

Thus, the method 400 enables combustion testing of a test material using the combustion test system 100 of FIGS. 1-3. Since the combustion test system 100 electrically isolates the charge storage device 128 from the power source 120 and other circuitry, changes in the power source 120 or other circuitry do not significantly affect the amount of energy that the charge storage device 128 can store. Thus, for example, a change in the power source 120 may not require performing an extensive re-calibration process to generate new calibration data 106 since the change in the power source 120 does not change the energy storage capacity of circuitry coupled to the first electrode 132 of the spark generation device 130.

Embodiments described above are illustrative and do not limit the disclosure. It is to be understood that numerous modifications and variations are possible in accordance with the principles of the present disclosure.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, the operations listed in the method 400 of FIG. 4 may be performed in a different order than illustrated, two or more of the operations may be performed concurrently (or combined), or one or more of the operations may be omitted. To illustrate, the electrical field strength data may be generated before the electrical arc is produced, such as concurrently with applying the voltage to the corona generator. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. A combustion test system comprising:
 a power source;
 a corona generator coupled to the power source;
 a charge storage device comprising a charging surface
  spaced apart from the corona generator such that charge carriers, motivated by an electric field of the corona generator, intersect the charging surface to charge the charge storage device;
a first electrode coupled to the charge storage device; and
a second electrode coupled to a reference ground and spaced apart from the first electrode to produce an electrical arc between the first electrode and the second electrode based on a voltage difference between the first electrode and the second electrode.

2. The combustion test system of claim 1, further comprising a test chamber around ends of the first electrode and the second electrode and configured to enclose a test material to be subjected to the electrical arc.

3. The combustion test system of claim 1, wherein the power source is configured to apply a time varying voltage to the corona generator.

4. The combustion test system of claim 1, wherein the charging surface is electrically isolated from the reference ground and from the power source enabling a voltage of the charging surface to float.

5. The combustion test system of claim 1, wherein the charge storage device comprises a capacitor including first capacitor electrode, a second capacitor electrode, and a dielectric material between the first capacitor electrode and the second capacitor electrode, wherein the first capacitor electrode includes the charging surface and the second capacitor electrode is coupled to the reference ground.

6. The combustion test system of claim 1, further comprising an electric field probe positioned to generate electric field strength data indicating an electric field strength of at least a portion of the electric field of the corona generator.

7. The combustion test system of claim 6, further comprising a processor and a memory accessible to the processor, the memory storing calibration data relating particular values of the electric field strength data to electrical energy levels of the electrical arc, and storing instructions executable by the processor to generate test result data based on the electric field strength data and the calibration data.

8. The combustion test system of claim 1, further comprising a trigger mechanism to initiate the electrical arc after the voltage difference between the first electrode and the second electrode satisfies a threshold.

9. The combustion test system of claim 8, wherein the trigger mechanism includes a source of excitation energy.

10. A method comprising:
storing charge at a charge storage device responsive to charge carriers directed toward the charge storage device, the charge carriers motivated by an electric field of a corona generator;
generating a voltage difference between a first electrode coupled to the charge storage device and a second electrode coupled to a reference ground; and
producing an electrical arc between the first electrode and the second electrode based on the voltage difference between the first electrode and the second electrode.

11. The method of claim 10, wherein the first electrode and the second electrode are disposed within a test chamber, and further comprising:
receiving a test material in the test chamber; and
subjecting the test material to the electrical arc.

12. The method of claim 10, further comprising applying a voltage to the corona generator to generate the electric field, wherein the electric field partially ionizes a gas to liberate the charge carriers.

13. The method of claim 12, wherein a polarity of the voltage alternates over time.

14. The method of claim 12, wherein a polarity of the voltage is constant over time.

15. The method of claim 10, further comprising generating, by an electric field probe, electric field strength data indicating an electric field strength of at least a portion of the electric field of the corona generator.

16. The method of claim 15, further comprising generating test result data based on the electric field strength data and calibration data that relates particular values of the electric field strength data to electrical energy levels of the electrical arc.

17. A spark generation device comprising:
a charge storage device comprising a charging surface configured to store charge responsive to charge carriers motivated by an electric field of a corona generator;
a first electrode coupled to the charge storage device; and
a second electrode coupled to a reference ground and spaced apart from the first electrode to produce an electrical arc between the first electrode and the second electrode based on a voltage difference between the first electrode and the second electrode.

18. The spark generation device of claim 17, further comprising a test chamber around ends of the first electrode and the second electrode and configured to enclose a test material to be subjected to the electrical arc.

19. The spark generation device of claim 17, wherein the charging surface is electrically isolated from the reference ground and from a power source of the corona generator.

20. The spark generation device of claim 17, wherein the charge storage device comprises a capacitor including first capacitor electrode, a second capacitor electrode, and a dielectric material between the first capacitor electrode and the second capacitor electrode, wherein the first capacitor electrode includes the charging surface and the second capacitor electrode is coupled to the reference ground.

* * * * *